United States Patent [19]

Otsuki et al.

[11] Patent Number: 4,515,979
[45] Date of Patent: May 7, 1985

[54] PREVENTION OF ODORS IN POLYORGANOSILOXANES

[75] Inventors: Masaaki Otsuki; Shinji Kida, both of Ohta, Japan

[73] Assignee: Toshiba Silicone Co., Ltd., Tokyo, Japan

[21] Appl. No.: 622,937

[22] Filed: Jun. 21, 1984

[30] Foreign Application Priority Data

Jul. 11, 1983 [JP] Japan ................................ 58-124669

[51] Int. Cl.³ ............................................... C07C 7/04
[52] U.S. Cl. ................................................. 556/445
[58] Field of Search ......................................... 556/445

[56] References Cited

U.S. PATENT DOCUMENTS

| | | | |
|---|---|---|---|
| 3,299,112 | 1/1967 | Bailey | 556/445 |
| 3,560,544 | 2/1971 | Haluska | 556/445 X |
| 3,629,308 | 12/1971 | Bailey et al. | 556/445 |
| 4,105,567 | 8/1978 | Koerner et al. | 556/445 X |

Primary Examiner—Paul F. Shaver
Attorney, Agent, or Firm—Gary L. Loser

[57] ABSTRACT

A process for preventing odor in a polyoxyalkylene group-containing polyorganosiloxane comprising adding phytic acid to the polyoxyalkylene group-containing polyorganosiloxane during and/or after its production.

5 Claims, No Drawings

PREVENTION OF ODORS IN POLYORGANOSILOXANES

The present patent application claims priority of Japanese patent application Ser. No. 83/124669, filed July 11, 1983.

BACKGROUND OF THE INVENTION

This invention relates to a process for preventing odor in a polyorganosiloxane. More particularly, the present invention relates to process for preventing odor in a polyoxyalkylene group-containing polyorganosiloxane which is used mainly as an additive in cosmetic compositions to impart thereto gloss, spread, smoothness, softness, and the like.

A liquid polyoxyalkylene group-containing polyorganosiloxane which is conventionally called a polyether-modified silicone fluid features excellent solubility in water and alcohol as well as excellent affinity for water, so that it has utility in a wide variety of industrial fields as an additive, for example, for cosmetic compositions, perfumery, and toiletries such as shampoo and hand cream. Among these fields of application, especially in the field of cosmetics, the liquid polyoxyalkylene group-containing polyorganosiloxane exhibits prominent versatility as an additive for imparting gloss, smoothness, softness, and the like, which are characteristic of a silicone.

The polyorganosiloxanes have such usefulness, however, have the following drawback. Namely, the polyoxyalkylene portion of the silicon is susceptible to oxidation, so that it is impossible to avoid odors caused by rancidity with the lapse of time. Moreover, in the production of the polyoxyalkylene group-containing polyorganosiloxane a polyoxyalkylene and a polyorganosiloxane are heated to form a copolymer, but in this case, oxidation of the polyoxyalkylene chain with air in the reactants also occurs concurrently, giving the product a faint rancid smell even just after production.

In recent years, because consumer's preferences for cosmetics are diverse and slightly perfuming cosmetics are preferred, as a matter of course, odorless or extremely low-odor materials are required for cosmetic preparations.

In reply to this requirement, a variety of studies and developments have been made and the following processes are known at present.

First, methods which are generally practices include, for example, a process in which an adsorbent such as active carbon or clay is used, and a process in which deodorization is performed by steam distillation in a deodorizing kettle, but these processes have the problem that although the product can be made low-odor just after the deodorization treatment, it is difficult to control subsequent odors due to rancidity with the lapse of time. Further, a process in which a phenolic compound is added as an antioxidant is known, but this process has a problem with respect to human safety.

Next, Japanese Patent Publication No. 41210/1980 discloses a process for preventing odors from a polyorganosiloxane, especially a water-soluble polyorganosiloxane due to rancidity with the lapse of time, which process comprises adding tocopherol, which is well known as Vitamin E. Although this process has no problem with respect to human safety, it has problems, for example, limited use, because the resulting cosmetics are colored owing to the marked coloring property of tocopherol. Thus the compound cannot satisfy a requirement of colorlessness or light color when it is used in cosmetics and, further, the cost of such cosmetics would be high since tocopherol itself is an extremely expensive material.

SUMMARY OF THE INVENTION

An object of this invention is to solve the above-mentioned problems and thereby provide a process for preventing odors in a polyoxyalkylene group-containing polyorganosiloxane and resulting in excellent storage stability.

The process for preventing smelling of a polyoxyalkylene group-containing polyorganosiloxane according to this invention is characterized by adding phytic acid during and/or after the production step of the polyoxyalkylene group-containing polyorganosiloxane.

DESCRIPTION OF THE INVENTION

The polyoxyalkylene group-containing polyorganosiloxane used in this invention is one that is ordinarily used as an additive or the like for cosmetics, and includes, for example, compounds represented by the following general formula:

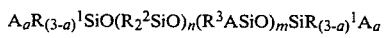

wherein A is a group represented by the general formula:

wherein $R^4$ is an alkylene group of 3 to 10 carbon atoms, or a group

$R^5$ is an alkylene group of 2 to 4 carbon atoms, $R^6$ is a hydrogen atom, or an alkyl group of 1 to 18 carbon atoms, and p is an integer of 3 to 70; $R^1$, $R^2$ and $R^3$ may be the same or different, and represent, independently, a member selected from the group consisting of a hydrogen atom, a hydrocarbon group of 1 to 20 carbon atoms and a halohydrocarbon group of 1 to 20 carbon atoms, a represents a number of 0 or 1, n represents a number of 0 to 180, m represents a number of 1 to 100, and $n+m$ represents a number of 1 to 200.

This polyoxyalkylene group-containing polyorganosiloxane is prepared, for example, by a process comprising effecting an addition reaction between a polyorganohydrogensiloxane represented by the general formula:

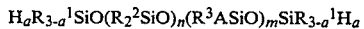

(wherein $R^1$, $R^2$, $R^3$, A, a, n, and m are as defined above) and a polyoxyalkylene represented by the general formula $R^7(OR^5)_pOR^6$ (wherein $R^5$, $R^6$ and p are as defined above and $R^7$ represents an alkylene group of 3 to 10 carbon atoms) in the presence of a catalyst such as chloroplatinic acid or a platinum complex compound, or by a process comprising effecting an addition reaction between the above polyorganohydrogensiloxane and an allylglycidyl ether in the presence of a similar catalyst, and then reacting the product with a polyoxyalkylene represented by the general formula:

in the presence of an acid catalyst.

In the above formulas, $R^1$, $R^2$ and $R^3$ may be the same or different, and include, for example, hydrogen atoms and, in addition, alkyl groups such as methyl, ethyl, propyl, butyl, pentyl, hexyl, heptyl, octyl, nonyl, decyl, dodecyl, and octadecyl; alkenyl groups such as vinyl and allyl; aralkyl groups such as β-phenylethyl and β-phenylpropyl; aryl groups such as phenyl; and halohydrocarbon groups such as 3,3,3-trifluoropropyl and chlorophenyl, but the methyl group is usually most suited because such a polyorganosiloxane best exhibits properties of a polyorganosiloxane, and can be synthesized easily. Examples of $R^4$ include the above-mentioned ether bond-containing bivalent groups and, in addition, propylene, butylene, pentylene, and hexylene, but a propylene group is most suited because the stability and water solubility of the polyoxyalkylene group-containing polyorganosiloxane are easily achieved. Examples of $R^5$ include, for example, ethylene, propylene, and butylene, but the ethylene or propylene group or a combination thereof are ordinarily used and, especially in order to render the polyorganosiloxane water-soluble, the ethylene group or a combination of the ethylene and propylene groups are preferred. Examples of $R^6$ include a hydrogen atom, and in addition, methyl and butyl groups.

Examples of $R^7$ in the polyoxyalkylene used in the synthesis include allyl, butenyl, pentenyl, and hexenyl, but the allyl group is most suited for the same reason as in the selection of $R^4$.

Phytic acid used in this invention is a hexaphosphate ester compound of myoinositol represented by the molecular formula $C_6H_{18}O_{24}P_6$, and is a compound which is known as a nontoxic natural product occurring in abundance in corns, seeds, and the like in the plant kingdom.

The amount of phytic acid used in this invention is preferably within the range of 10 to 5,000 ppm, preferably 50 to 500 ppm, based on the polyorganosiloxane. When this amount is smaller than the lower limit of the above range, the effect of preventing odor is not sufficient, whereas when this amount is excessive, no effect corresponding to the amount used can be expected, and conversely coloration due to phytic acid itself increases, which is not desirable. Although phytic acid itself is usually light yellow or light brown, it scarcely colors products when it is added in an amount within the above range.

In this invention, phytic acid may be added in any stage, i.e., during and/or after the step of producing the polyorganosiloxane from its intermediates, but from the viewpoint of preventing odors from the polyoxyalkylene groups due to rancidity during production, the step of producing it from intermediates is preferred.

This invention will now be described in more detail with reference to examples of this invention. In these examples parts are all parts by weight.

EXAMPLES

EXAMPLES 1 TO 7

A four-necked flask equipped with a dropping funnel, agitator, reflux condenser with a dehydrator, and thermometer was charged with 350 parts of a polyoxyethylene group-containing polyoxyethylene monoallyl ether having one hydroxyl group-blocked end (average molecular weight of 400) and 200 parts of toluene. To this was added 0.11 part of a 50% aqueous solution of phytic acid (0.055 part in terms of phytic acid), and the whole mixture was heated under conditions of refluxing toluene to remove water. Then, to this mixture was added 0.055 part of sodium acetate as a pH adjusting agent, and an isopropanol solution of chloroplatinic acid in such an amount as to provide 2 ppm, by weight, of platinum based on the above polyoxyethylene monoallyl ether. 200 parts of a trimethylsilyl-terminated polymethylhydrogensiloxane containing four (average per molecule) methylhydrogensiloxane units and twelve (average per molecule) dimethylsiloxane units was added drop-wise to the mixture from the dropping funnel, while the mixture was maintained at 100° C. Here the amount of polymethylhydrogensiloxane in relation to that of the polyoxyethylene allyl ether was determined from the content of hydrogen atoms in the former which were to react with the allyl groups of the former. After completion of the addition, agitation was continued for 4 hours at a temperature of 100° C. to complete the reaction. Then, the toluene and the other volatile components were removed by maintaining the mixture after the reaction at 120° C. and 200 mm Hg for one hour. The residue was filtered by suction under pressure with the help of a filter aid of diatomaceous earth to obtain a sample of polyoxyalkylene group-containing polyorganosiloxane (referred to simply as siloxane in the Table. Here the siloxane is referred to as (A).

Samples containing siloxane (A) were prepared (Examples 3, 4, and 5) by similar reactions in which the amount of phytic acid was varied. Further, siloxanes (B) and (C) were synthesized (Examples 2 and 6) by varying the kinds of polymethylhydrogensiloxane and polyoxyalkylene and determining their amounts in the manner as described above and carrying out the synthesis in the presence of phytic acid. Further, siloxane (D) was synthesized (Example 7) by heating a polyoxyalkylene and a corresponding allyl glycidyl ether-added polysiloxane under agitation for 4 hours at the reflux temperature of toluene in the presence of toluene, a boron trifluoride/ether adduct in an amount of 0.5% based on the polymers, and phytic acid, and carrying out solvent removal and filtration in the same manner as in Example 1.

Similar procedures were followed to prepare samples of polyoxyalkylene group-containing polyorganosiloxane (Examples 2 to 7) having the compositions shown in the Table and different amounts of phytic acid.

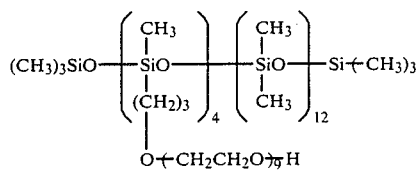

(A)

(B)
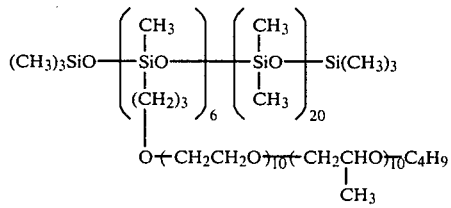

(C)
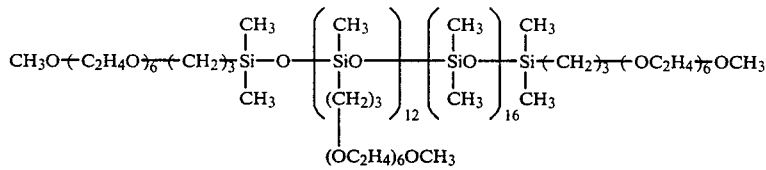

(D)
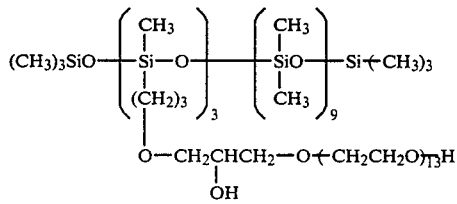

COMPARATIVE EXAMPLES 1 TO 4

Samples of polyoxyalkylene group-containing polyorganosiloxane (A) to (D) were prepared in the same way except that no phytic acid was used in the Examples.

The samples of Examples 1 to 7 and those of comparative Examples 1 to 4 were examined for odor and appearance just after production, and for odor and formaldehyde concentrations (Kitagawa's gas detector tube) after 6-months storage at 40° C., The Table shows the results.

taining polyorganosiloxane during and/or after its production.

2. A process for preventing odor in a polyoxyalkylene group-containing polyorganosiloxane as set forth in claim 1, wherein said polyoxyalkylene group-containing polyorganosiloxane is a compound represented by the general formula:

$$A_aR_{(3-a)}{}^1SiO(R_2{}^2SiO)_n(R^3ASiO)_mSiR_{(3-a)}{}^1A_a$$

wherein A is a group represented by the general formula $-R^4(OR^5)_pOR^6$, wherein $R^4$ is an alkylene group

TABLE

|  | Example |  |  |  |  |  |  | Comparative Example |  |  |  |
|---|---|---|---|---|---|---|---|---|---|---|---|
|  | 1 | 2 | 3 | 4 | 5 | 6 | 7 | 1 | 2 | 3 | 4 |
| Structural formula of siloxane | (A) | (B) | (A) | (A) | (A) | (C) | (D) | (A) | (B) | (C) | (D) |
| Amount of phytic acid part (ppm) based on siloxane | 100 | 200 | 10 | 50 | 500 | 100 | 100 | 0 | 0 | 0 | 0 |
| Smell just after production | very slight | very slight | very slight | very slight | very slight | very slight | very slight | slight rancid | slight rancid | slight rancid | slight rancid |
| Smell after a 6-month storage at 40° C. | very slight | very slight | slight rancid | very slight | very slight | very slight | very slight | strong rancid | strong rancid | strong rancid | strong rancid |
| Formaldehyde concentration by Kitagawa's gas detector tube | <1 ppm | <1 ppm | 2 ppm | <1 ppm | <1 ppm | <1 ppm | <1 ppm | 15 ppm | 20 ppm | 25 ppm | 20 ppm |

As described above in detail, the poloxyalkylene group-containing polyorganosiloxane according to the present invention is excellent in storage stability and has great industrial value.

We claim:

1. A process for preventing odor in a polyoxyalkylene group-containing polyorganosiloxane comprising adding phytic acid to the polyoxyalkylene group-conof 3 to 10 carbon atoms, or a group $-(CH_2)_3-O-CH_2CH(OH)CH_2-$, $R^5$ is an alkylene group of 2 to 4 carbon atoms, $R^6$ is a hydrogen atom or an alkyl group of 1 to 18 carbon atoms, and p represents an integer of 3 to 70, $R^1$, $R^2$ and $R^3$ may be the same or different and represent, independently, a member selected from the group consisting of a hydrogen atom, a hydrocarbon group of 1 to 20 carbon atoms and a halohydrocarbon group of 1 to 20 carbon atoms, a represents a number of 0 or 1, n represents a number of 0 to 180, m represents a number of 1 to 100, and n+m represents a number of 1 to 200.

3. A process for preventing odor in a polyoxyalkylene group-containing polyorganosiloxane as set forth in claim 1, wherein said polyoxyalkylene group-containing polyorganosiloxane is water-soluble.

4. A process for preventing odor in a polyoxyalkylene group-containing polyorganosiloxane as set forth in claim 1, wherein the amount of phytic acid used is 50 ppm to 500 ppm, based on the polyoxyalkylene group-containing polyorganosiloxane.

5. A process for preventing odor in a polyoxyalkylene group-containing polyorganosiloxane as set forth in claim 1, wherein the amount of phytic acid is added to said polyoxyalkylene group-containing polyorganosiloxane during its production from a polyorganohydrogensiloxane or allylglycidyl ether adduct thereof and a polyoxyalkylene.

* * * * *